(12) United States Patent
Grimm et al.

(10) Patent No.: US 8,663,234 B2
(45) Date of Patent: Mar. 4, 2014

(54) COMBINATION LIGAMENT TENSIONER AND ALIGNMENT DEVICE

(75) Inventors: James Grimm, Winona Lake, IN (US); Anthony Romano, Columbia City, IN (US)

(73) Assignee: Zimmer, Inc., Warsaw, IN (US)

( * ) Notice: Subject to any disclaimer, the term of this patent is extended or adjusted under 35 U.S.C. 154(b) by 56 days.

(21) Appl. No.: 13/195,604

(22) Filed: Aug. 1, 2011

(65) Prior Publication Data

US 2013/0035694 A1    Feb. 7, 2013

(51) Int. Cl.
*A61B 17/02* (2006.01)
*A61F 2/46* (2006.01)

(52) U.S. Cl.
USPC .............................. 606/102; 606/90; 606/105

(58) Field of Classification Search
USPC ..................... 606/86 R, 87, 88, 90, 102, 105; 33/501.05, 501.08–501.09, 501.1, 33/501.3, 501.45, 501.5, 512, 542, 544.5; 433/72
See application file for complete search history.

(56) References Cited

U.S. PATENT DOCUMENTS

| | | | |
|---|---|---|---|
| 987,703 A | 3/1911 | Curtin | |
| 1,524,474 A | 1/1925 | Buck | |
| 1,661,701 A | 3/1928 | Michler | |
| 2,498,171 A | 2/1950 | Michler | |
| 3,063,153 A | 11/1962 | Stites | |
| 3,816,010 A | 6/1974 | DiRago | |
| 4,498,239 A | 2/1985 | Epstein | |
| 4,517,747 A * | 5/1985 | Morin | 33/512 |
| 4,571,181 A | 2/1986 | Berger | |
| 4,654,005 A | 3/1987 | Woelfel | |
| 5,213,112 A | 5/1993 | Niwa et al. | |
| 5,456,695 A * | 10/1995 | Herve Dallemagne | 606/207 |
| 5,649,929 A | 7/1997 | Callaway | |
| 5,810,831 A | 9/1998 | D'Antonio | |
| 6,413,086 B1 | 7/2002 | Womack | |
| 6,673,077 B1 | 1/2004 | Katz | |

(Continued)

FOREIGN PATENT DOCUMENTS

| | | |
|---|---|---|
| EP | 1707159 A1 | 10/2006 |
| EP | 1821062 A2 | 8/2007 |
| WO | WO-2005051242 A1 | 6/2005 |
| WO | WO-2013019803 A1 | 2/2013 |

OTHER PUBLICATIONS

"International Application Serial No. PCT/US2012/049016, International Search Report mailed Jan. 15, 2013", 6 pgs.

(Continued)

*Primary Examiner* — Michael T Schaper
*Assistant Examiner* — Tracy Kamikawa
(74) *Attorney, Agent, or Firm* — Schwegman, Lundberg & Woessner, P.A.

(57) ABSTRACT

A feeler gauge and alignment device comprises a first outer shim having a first end, a second end, and an alignment aperture disposed between the first end and the second end, a second outer shim having a first end, a second end, and an alignment aperture disposed between the first end and the second end, and one or more inner shims disposed between the first outer shim and the second outer shim, each of the one or more inner shims having a first end, a second end, and an alignment aperture disposed between the first end and the second end. The first outer shim, the second outer shim, and the one or more inner shims are rotatably coupled about the first ends.

7 Claims, 13 Drawing Sheets

(56) References Cited

U.S. PATENT DOCUMENTS

| | | |
|---|---|---|
| 7,285,122 B2 | 10/2007 | Sanford et al. |
| 7,618,451 B2 | 11/2009 | Berez et al. |
| 7,842,039 B2 | 11/2010 | Hodorek et al. |
| 7,849,633 B2 | 12/2010 | Oshima et al. |
| 2003/0153924 A1 | 8/2003 | Kana et al. |
| 2004/0210317 A1 | 10/2004 | Maroney et al. |
| 2005/0143744 A1 | 6/2005 | Keeven et al. |
| 2005/0149038 A1 | 7/2005 | Haines et al. |
| 2007/0162036 A1 | 7/2007 | Schifrine et al. |
| 2007/0198022 A1 | 8/2007 | Lang et al. |
| 2008/0015607 A1 | 1/2008 | D'Alessio et al. |
| 2008/0281329 A1 | 11/2008 | Fitz et al. |
| 2008/0281426 A1 | 11/2008 | Fitz et al. |
| 2008/0306484 A1 | 12/2008 | Coon et al. |
| 2009/0125114 A1* | 5/2009 | May et al. .................. 623/20.14 |
| 2009/0222014 A1 | 9/2009 | Bojarski et al. |
| 2010/0217156 A1 | 8/2010 | Fisher et al. |
| 2010/0286699 A1 | 11/2010 | Berger et al. |
| 2010/0305573 A1 | 12/2010 | Fitz et al. |
| 2010/0305574 A1 | 12/2010 | Fitz et al. |
| 2011/0004316 A1 | 1/2011 | Murray et al. |
| 2012/0310246 A1* | 12/2012 | Belcher et al. .................. 606/80 |

OTHER PUBLICATIONS

"International Application Serial No. PCT/US2012/049016, Invitation to Pay Additional Fees mailed Oct. 25, 2012", 7 pgs.

"International Application Serial No. PCT/US2012/049016, Written Opinion mailed Jan. 15, 2013", 8 pgs.

\* cited by examiner

COMBINATION LIGAMENT TENSIONER AND ALIGNMENT DEVICE

BACKGROUND

The present patent application relates to unicondylar knee arthroplasty, and, more particularly, to an apparatus and method for achieving correct limb alignment and ligament tension during a knee replacement procedure.

Orthopedic procedures for the replacement of all, or a portion of, a patient's joint have been developed over the last thirty years. Currently, the procedures used to prepare the bone and seat the implants are generally referred to as open procedures. For the purposes of this discussion, the term "open procedure" will refer to a procedure wherein an incision is made through the skin and underlying tissue to fully expose a large portion of the particular joint surface. In both total and unicondylar knee arthroplasty, the typical incision for an open procedure can be about 8-10 inches long. After the initial incision in the skin, the internal wound can be enlarged to fully expose the areas to be prepared. While this approach provides surgeons with an excellent view of the bone surface, the underlying damage to the soft tissue, including the muscles, can lengthen a patient's rehabilitation time after surgery. While the implants may be well fixed at the time of surgery, it may be several weeks or perhaps months before the tissues violated during surgery are fully healed.

Unicompartmental knee arthroplasty can be utilized to correct a varus or a valgus deformity caused by, e.g., osteoarthritis affecting the medial (a varus deformity) or lateral (a valgus deformity) compartment of the knee. Traditionally, unicondylar knee arthroplasty is an open procedure in which a surgeon, after exposing the knee, resects diseased or otherwise undesirable bone from the appropriate compartment of the knee, including portions of the distal femur and the proximal tibia. The distal femur and proximal tibia of the affected compartment are also shaped to receive a unicondylar knee prosthesis.

In traditional unicondylar knee arthroplasty, leg alignment requires a trial and error technique in which the surgeon makes one of the distal femoral cut and the proximal tibial cut and thereafter selects the location of the other of the distal femoral cut and the proximal tibial cut based on experience and the knowledge that tibial prostheses are available in a limited number of thicknesses. Typically, the proximal tibial cut is made so as to remove the least amount of the proximal tibia, while ensuring sufficient removal of diseased or otherwise undesirable bone. The remaining femoral cuts can be made to complete shaping of the femur to receive a femoral prosthesis. After the femoral and tibial cuts are complete, the femoral prosthesis and the tibial prosthesis, or provisional versions thereof, can be temporarily implanted and leg alignment reviewed by the surgeon. If the tibial prosthesis does not include an integral bearing component, then a discrete bearing component can also be implanted. To adjust leg alignment, the surgeon can replace the tibial prosthesis or bearing component with an alternative tibial prosthesis or bearing component having an increased or decreased thickness. The surgeon can also recut the femur and/or use a different femoral implant to achieve appropriate leg alignment. Additionally or alternatively, the surgeon can remove more tibial bone stock and again insert the previously used tibial prosthesis, or replace the previously used tibial prosthesis with a tibial prosthesis of a different thickness. This procedure of trial and error can be conducted until the surgeon believes that appropriate leg alignment and soft tissue tension has been achieved.

OVERVIEW

This overview is intended to provide an overview of subject matter of the present patent application. It is not intended to provide an exclusive or exhaustive explanation of the invention. The detailed description is included to provide further information about the present patent application.

The present inventors have recognized, among other things, that the traditional trial and error technique utilized in performing unicompartmental knee arthroplasty is tedious and time consuming, and could result in excessive removal of tibial and/or femoral bone. Thus, the present inventors have recognized that what is needed in the art is a multi-function device that allows the surgeon to quickly and easily assess the resected gaps in the knee joint while also allowing the surgeon to verify proper alignment of the knee joint with respect to a center of the ankle. Providing multiple functions in a single, easy-to-use device can greatly reduce the amount of time necessary for a surgeon to select the appropriate prosthesis components, as well as the amount of unnecessary bone that is removed from the tibia and/or femur.

In an example a feeler gauge and alignment device can be provided that includes a first outer shim having a first end, a second end, and an alignment aperture disposed between the first end and the second end, a second outer shim having a first end, a second end, and an alignment aperture disposed between the first end and the second end, and one or more inner shims disposed between the first outer shim and the second outer shim, each of the one or more inner shims having a first end, a second end, and an alignment aperture disposed between the first end and the second end. The first outer shim, the second outer shim, and the one or more inner shims are rotatably coupled about the first ends.

In an example a method for analyzing characteristics of a knee joint is provided that includes inserting, into a knee joint to measure a resection gap, one or more shims of a feeler gauge and alignment device having a plurality of shims, inserting an alignment rod through an alignment channel formed in one or more of the shims, and verifying a desired alignment of a tibia with respect to the knee joint such as by using the inserted alignment rod. Each of the shims can include a first end, a second end, and a shim thickness, and the shims are rotatably coupled about the first ends.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present patent application relates to devices and methods for measuring resection gaps and verifying joint alignment during a knee arthroplasty procedure. During a typical arthroplasty procedure, an incision is made into the knee joint to expose the bones comprising the joint. Cutting guides can then be used to guide the removal of the articular surfaces that are to be replaced. In order to help the surgeon decide upon the appropriate artificial joint components for replacing the resected bone ends, a feeler gauge and alignment device can be used to measure various gaps created by the resections and verify the desired alignment and mechanics of the joint.

Figure 1:
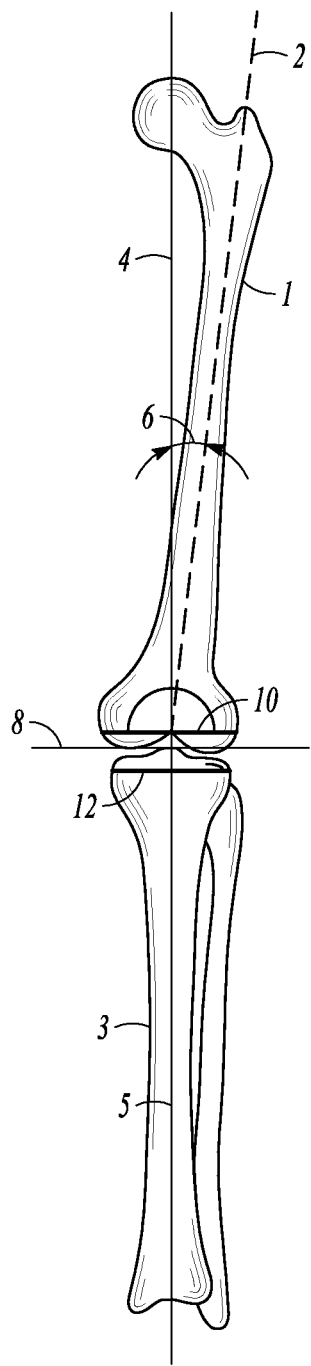
FIG. 1 is a front elevation view of a tibia and a femur showing axes of a knee joint.
Figure 2:
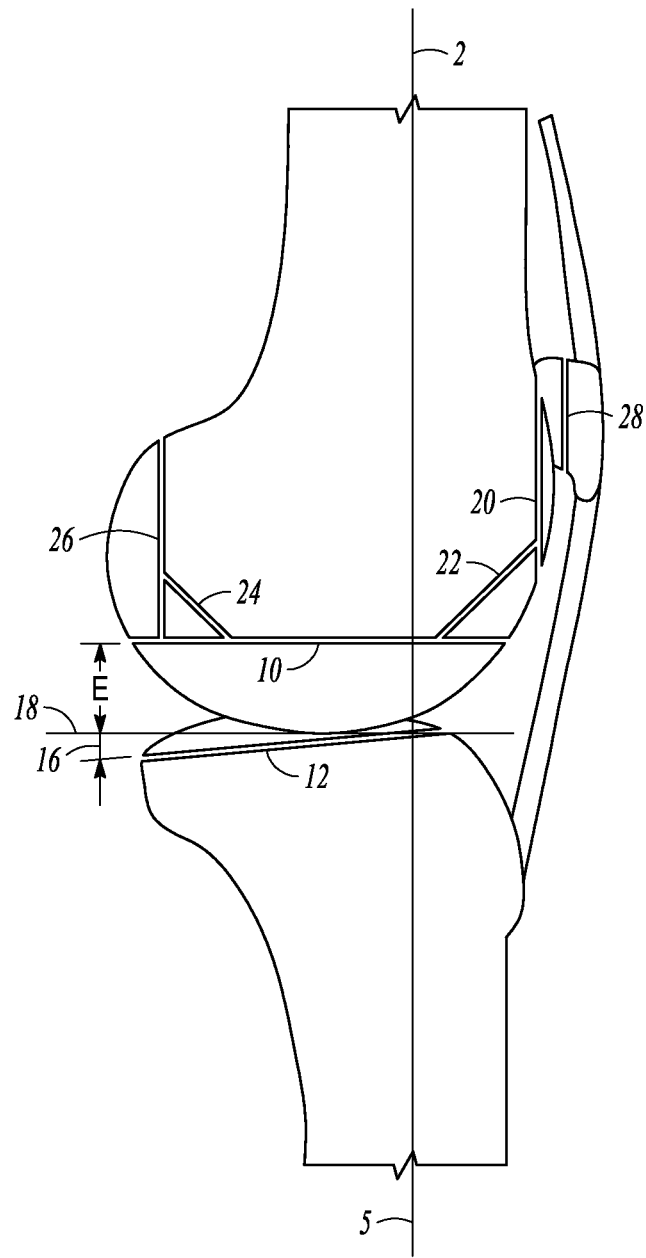
FIG. 2 is a side section view of a knee joint showing typical bone cuts used in replacing joint surfaces.
Figure 3:
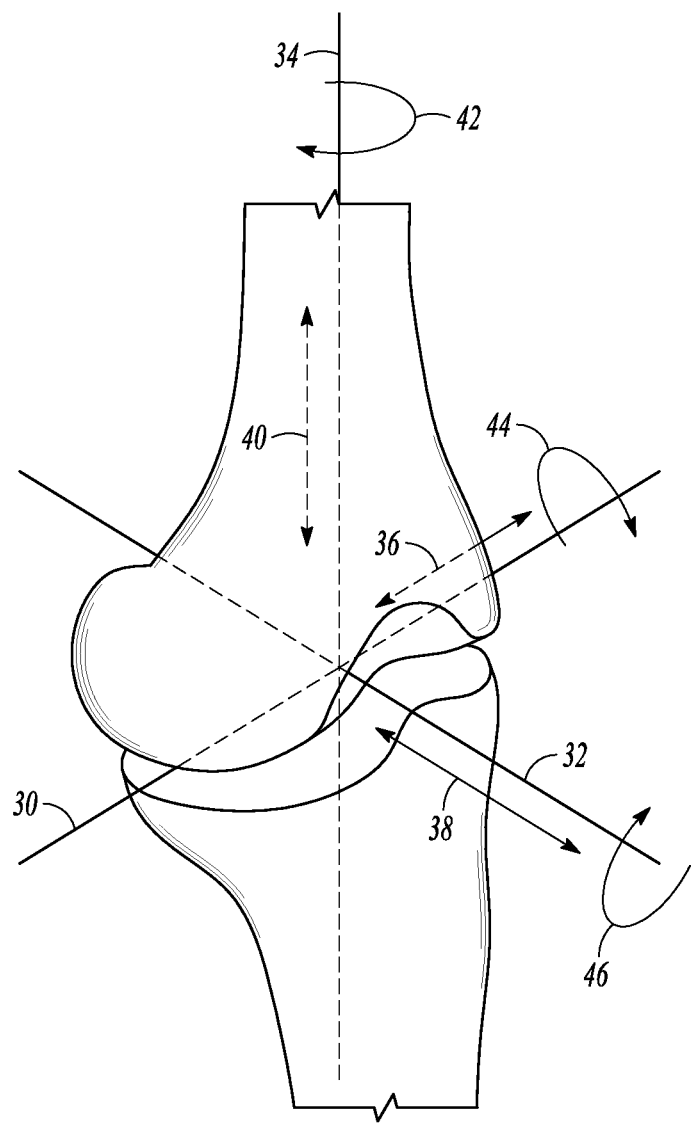
FIG. 3 is a perspective view of a knee joint showing aspects of component positioning.

In order to better understand knee arthroplasty procedures, it is helpful to understand the relationship of the bones and the cuts made to orient the various implant components. FIGS. 1-3 illustrate several aspects of implant orientation. Beginning with FIG. 1, a diagram of the lower limb in the frontal plane is presented to illustrate various axes of the lower limb. For example, the femur 1 has an anatomic axis 2 coinciding generally with its intramedullary canal. The femur 1 also has a mechanical axis 4, or load axis, running from the center of the femoral head to the center of the knee. The angle 6 between these two axes varies within the patient population but is generally on the order of 6 degrees. Likewise, the tibia 3 has an anatomic axis coinciding generally with its intramedullary canal. The mechanical axis 5 of the tibia 3 runs from the center of the knee to the center of the ankle and is generally collinear with the anatomic axis. The transverse axis, or joint line 8, about which the knee flexes, is parallel to a line through the medial and lateral femoral condyles and parallel to the tibial plateau. This line subtends a slight valgus angle of approximately 87 degrees with the mechanical axis 4 of the femur 1 and a slight varus angle of approximately 87 degrees with the mechanical axis 5 of the tibia 3. Thus, the distal femur is in slight valgus and the proximal tibia is in slight varus. Normally, portions of the distal femur and proximal tibia are resected to be parallel to the joint line 8, and thus perpendicular to the mechanical axis 4, as indicated at 10 and 12. The intersection of the femoral and tibial mechanical axes, 4 and 5, can subtend an angle relative to one another. However, the angle is small and the mechanical axis 4 of the femur 1 has an approximately normal alignment with the proximal tibia if the knee is uninjured. Therefore the tibial mechanical axis 5 can be extrapolated to the distal femur to determine the femoral mechanical axis 4 in the distal femur when there is a femoral deformity. Similarly, if there is a deformity in the tibia 3, the mechanical axis 5 of the proximal tibia 3 can be determined such as by extrapolating the femoral mechanical axis.

FIG. 2 illustrates the knee joint from the side or sagittal view and various bone cuts that can be made to align implant components. The distal femur can be cut 10 perpendicular, in the anterior-to-posterior direction, to the anatomic axis 2 of the femur. The proximal tibial resection 12 can be cut to match the natural posterior slope of the proximal tibia relative to the tibial mechanical axis 5. The amount of posterior slope 16 relative to a reference line 18 perpendicular to the tibial mechanical axis 5 varies in the patient population but is typically on the order of about 7 degrees. The distance between the distal femoral 10 and proximal tibial 12 cuts along the mechanical axes 4 and 5 is the extension gap E. Other cuts can be made depending on the components that are to be implanted. These can include an anterior femoral cut 20, an anterior femoral chamfer cut 22, a posterior femoral chamfer cut 24, and a posterior femoral cut 26. The patella 7 can also be cut 28 to allow for replacement of the patellar articular surface. Additional preparation of the bone can include drilling or notching the bones to receive pegs, stems, and other extensions from the components (not shown). However, for purposes of simplicity, the following disclosure is limited to discussion of the distal femoral 10 and proximal tibial 12 cuts.

FIG. 3 depicts six aspects of component positioning relative to a coordinate system in which the x-axis 30 corresponds approximately to the joint line 8, the z-axis 34 corresponds approximately to the mechanical axes 4 and 5, and the y-axis 32 is normal to the other two. Position along each of these axes is depicted by arrows. Particularly, position along the x-, y-, and z-axes determines the medial/lateral (dx) 36, anterior/posterior (dy) 38, and proximal/distal (dz) 40 positioning of components, respectively. Rotation about each of these axes is also depicted by arrows. Rotation about the z-axis (rz) 42 corresponds anatomically to external rotation of the femoral component, while rotation about the x-axis (rx) 44 and y-axis (ry) 46 corresponds to extension plane slope and varus/valgus angle, respectively. Depending on the order of the cuts, and the way that subsequent instruments reference each cut, the position of the distal femoral cut 10 can affect the location of the joint line (dz), the extension gap, the varus/valgus angle (ry), and the extension plane angle (rx). Likewise, the position of the proximal tibial cut 12 can affect the varus/valgus angle (ry), extension plane (rx), external rotation (rz), and the joint line (dz) or extension gap.

Figure 6:
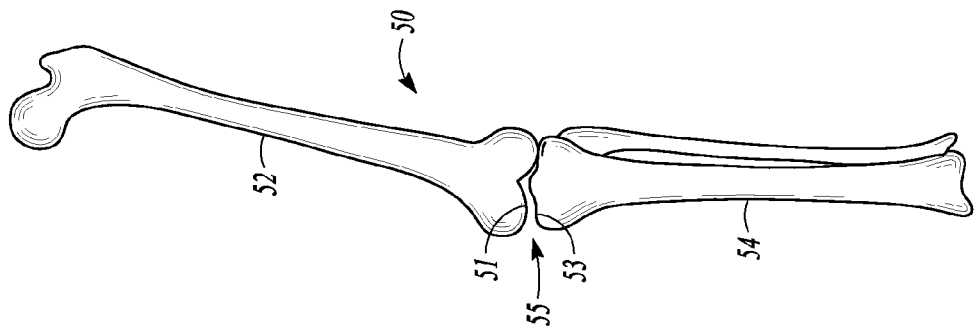
FIGS. 4, 5, and 6 are front elevation views illustrating a knee joint with normal or neutral pre-surgical limb alignment, varus pre-surgical limb alignment, and valgus pre-surgical limb alignment, respectively.
Figure 5:
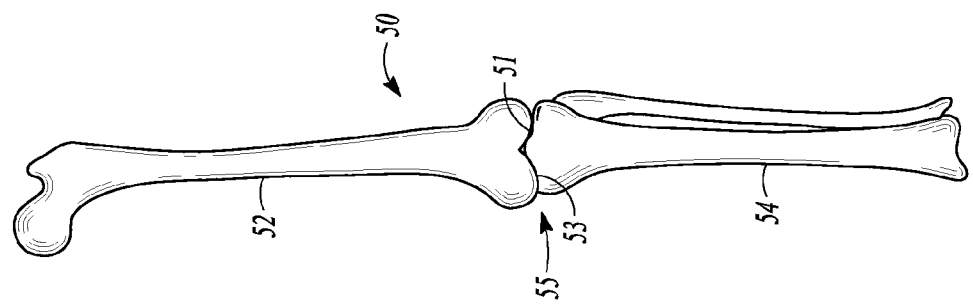
Figure 4:
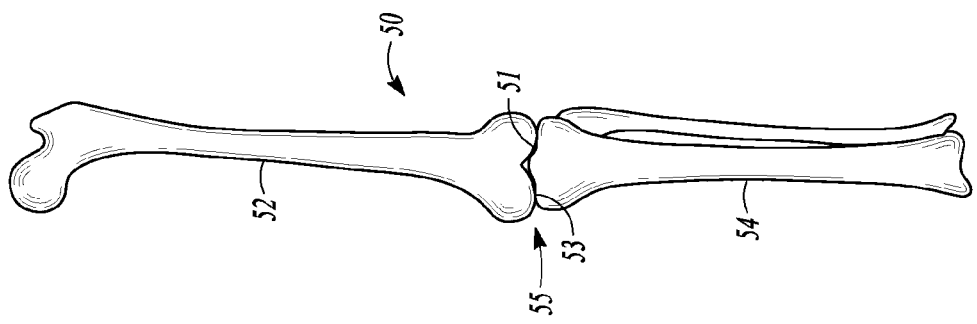

FIGS. 4, 5, and 6 are front elevation views illustrating a knee joint 50 with normal or neutral pre-surgical limb alignment, varus pre-surgical limb alignment, and valgus pre-surgical limb alignment, respectively. The knee joint 50 can be formed by portions of a distal end 51 of a femur 52 and a proximal end 53 of a tibia 54. Assuming that the surgeon's goal is to maintain or achieve "neutral" limb alignment in each of these three examples, with reference to the "neutral" example in FIG. 4 the surgeon would select a tibial cut depth and tibial implant on the medial side 55 of the knee joint 50 that maintains the joint line 8 (FIG. 1) roughly at its current location. With reference to the "varus" example in FIG. 5, the surgeon would select a tibial cut depth and tibial implant on the medial side 55 of the knee joint 50 that raises the joint line 8 (FIG. 1) from its current location. Finally, with reference to the "valgus" example in FIG. 6, the surgeon would select a tibial cut depth and tibial implant on the medial side 55 of the knee joint 50 that lowers the joint line 8 (FIG. 1) from its current location. Correction of the knee joint 50 would also involve, at a minimum, one or more femoral cuts. Establishing a neutral limb alignment may not always be desirable. For example, a surgeon may decide that with a particular patient establishing a mechanical axis that results in a slightly varus or a slightly valgus knee is preferable.

Now that a general overview of knee arthroplasty procedures has been provided, the feeler gauge and alignment device in accordance with the subject matter of the present patent application will be described in detail. For purposes of example and not limitation, the feeler gauge and alignment device will be illustrated and described with reference to a unicondylar knee procedure in which a single compartment of the knee joint is replaced including a portion of one femoral condyle and a portion of the proximal tibia. However, it is contemplated that feeler gauge and alignment devices in accordance with the present disclosure can also be used in a total knee replacement procedure in which both the medial and lateral portions of the knee joint are resurfaced.

Figure 7:
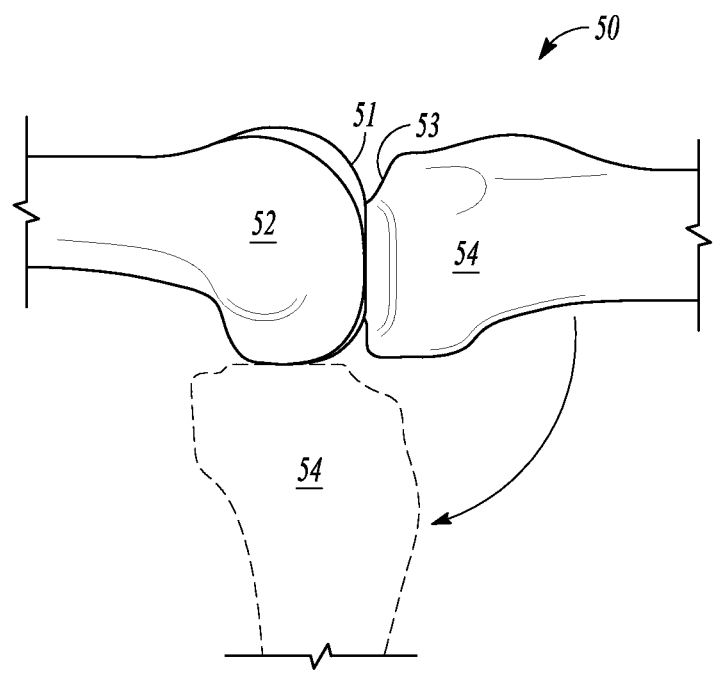
FIG. 7 is a diagram illustrating a knee joint prior to beginning a unicondylar knee replacement procedure.

FIG. 7 is a diagram illustrating the knee joint 50 prior to beginning the unicondylar knee replacement procedure. The knee joint 50 is movable from a position of "extension" as depicted by the solid line tibia 54 to a position of "flexion" as indicated by the broken line tibia 54. For purposes of clarity and simplicity of illustration, the distal end 51 of the femur 52 and the proximal end 53 of the tibia 54 are not depicted with the type of damage that would typically be found in a patient in need of a knee replacement (full or partial). However, one or both of the distal end 51 of the femur 52 and the proximal end 53 of the tibia 54 would contain damaged bone and/or tissue, thus necessitating surgery.

Figure 8:
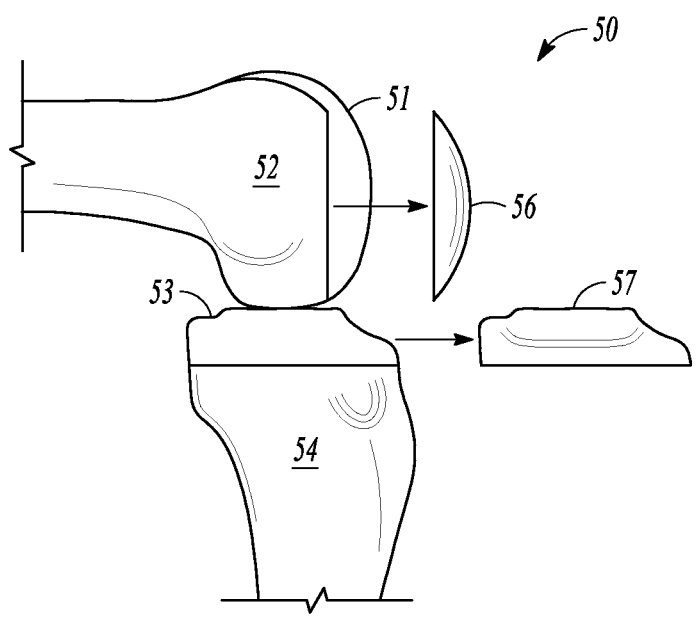
FIG. 8 is a diagram illustrating the knee joint of FIG. 7 with a distal portion of a medial femoral condyle and a proximal portion of a tibia resected from the knee.

One goal of unicondylar knee surgery can be to resect portions of the distal end 51 of the femur 52 and the proximal end 53 of the tibia 54 and replace those portions with femoral and tibial knee replacement components. These femoral and tibial knee replacement components function to, among other things, restore operation of the patent's knee joint and relieve pain. To that end, FIG. 8 is a diagram illustrating a distal portion 56 of the medial femoral condyle and a proximal portion 57 of the tibia 54 that have been resected using any suitable resection technique. For example, the femoral and tibial resections can be performed using a saw blade and a corresponding guide, with the knee joint 50 in flexion or extension. The resection procedure can involve preoperative planning steps that are performed prior to the surgery, using images of the patient's knee, in order to determine the desired locations for the various cuts. In an example, the resection procedure can begin without any preoperative planning steps, such as by forming an incision in the tissue surrounding the knee joint 50 and making decisions regarding the locations of the femoral and tibial cuts based upon the judgment of the surgeon. Whether preoperative planning is involved or not, the resection procedures commonly begin with resecting a "standard" or "predetermined" amount of bone from the proximial end 53 of the tibia 54. In one example, the proximal portion 57 of the tibia 54 resected by the surgeon may have a thickness of about 8 mm in order to allow for implantation of an 8 mm knee replacement implant within the knee joint. This example of a scenario, where a predetermined amount of bone is resected from the knee joint and replaced with an implant of the same thickness, assumes that the surface on the proximal end 53 of the tibia 54 has not been damaged to the point where a portion of the bone has already been worn away. If a portion of the bone surface has in fact been worn away, then the surgeon can instead resect enough additional bone material to allow for use of the desired implant, such as the 8 mm knee implant in the above example.

The above resections are described merely for purposes of example and not limitation. The manner of making resections, the order of the resections, and the dimensions of the resections are not critical to the operation of the feeler gauge and alignment device.

Regardless of the surgical method used to resect the distal portion 56 of the femur 52 and the proximal portion 57 of the tibia 54, it may be desirable to measure various gaps within the knee joint 50 throughout the resection procedure in order to help determine (or confirm) the appropriate size of replacement knee implant for use in the patient. As alluded to above, replacement knee implants typically include a femoral implant component and a tibial implant component. Often times, the replacement knee implants provide one femoral implant component of a fixed thickness and a number of tibial implant components having a range of thicknesses. By providing a single "choice" for the femoral implant component, the only variable that involves consideration by the surgeon is the appropriate size of the tibial implant component that produces the desired amount of correction. As will be described in further detail to follow, gap measurements taken within the resected knee joint can be used to determine which of the tibial implant components to use with the femoral implant component.

Figure 9:
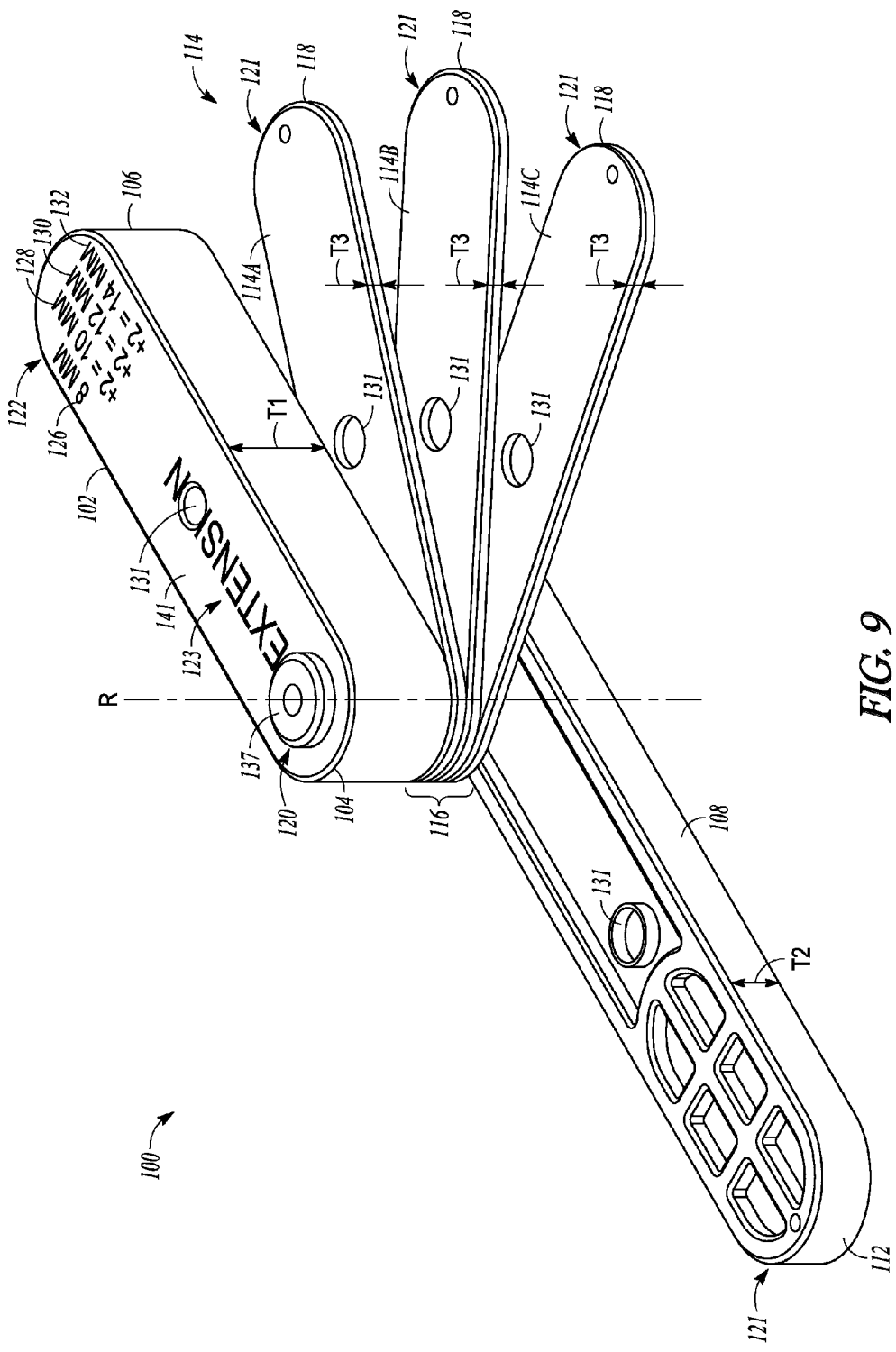
FIGS. 9 and 10 are perspective views of one example of a feeler gauge and alignment device in accordance with the present patent application.
Figure 10:
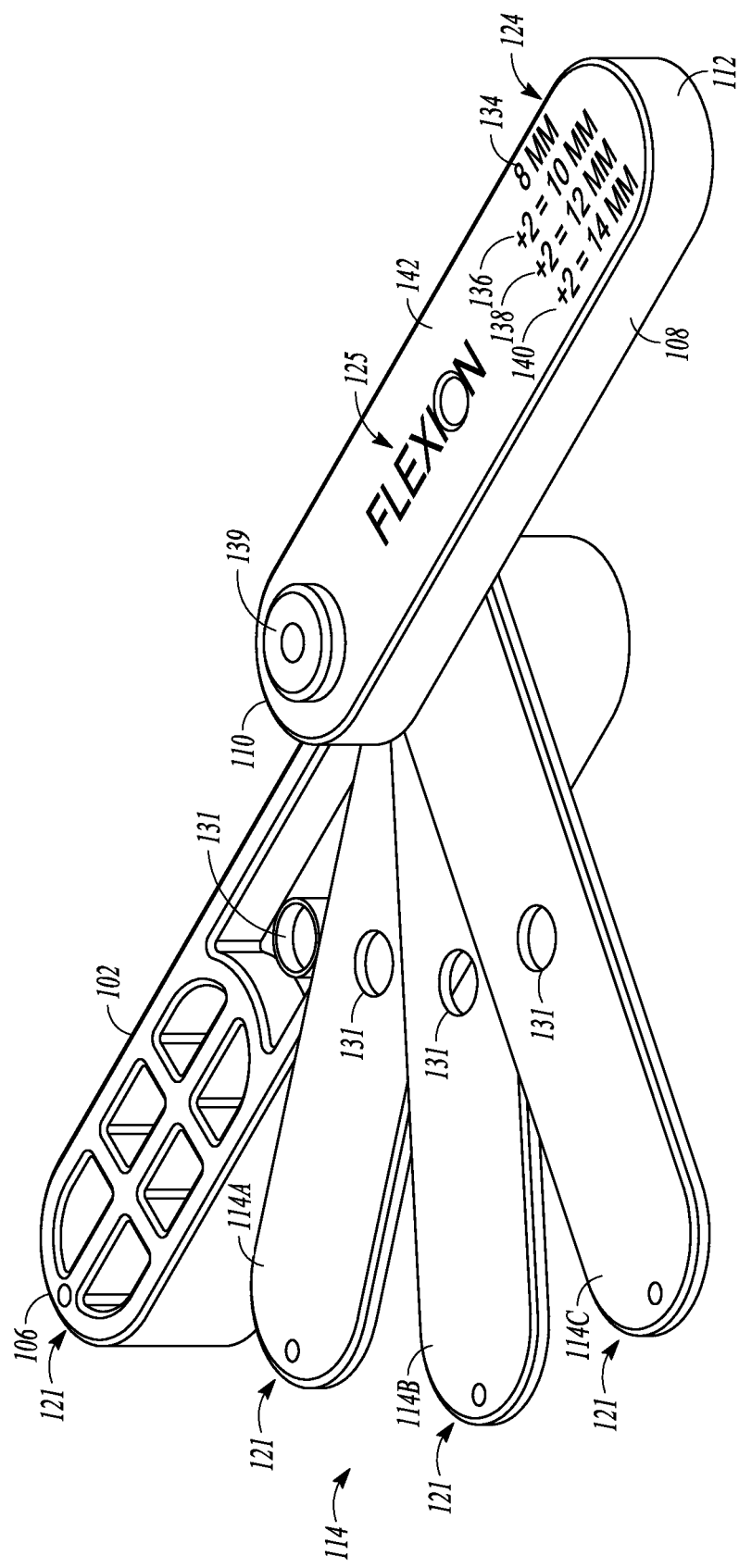

FIGS. 9 and 10 are perspective views from two opposing sides of a feeler gauge and alignment device 100. As illustrated in FIGS. 9 and 10, the feeler gauge and alignment device 100 generally includes a first outer shim 102 having a first end 104 and a second end 106, a second outer shim 108 having a first end 110 and a second end 112, and one or more inner shims 114 disposed between the first outer shim 102 and the second outer shim 108, each of the one or more inner shims 114 including a first end 116 and a second end 118. With reference to FIGS. 9 and 10, three inner shims 114A-114C are illustrated and described herein for purposes of example.

As shown in FIG. 9, the first outer shim 102 has a first shim thickness T1. The second outer shim 108 has a second shim thickness T2. Finally, the inner shims 114A-114C have thicknesses T3. Optionally but not necessarily, the thicknesses of the shims can be substantially constant between their respective first and second ends. In one example as will be described herein, the thickness T1 can be about 8 mm, the thickness T2 can be about 6 mm, and the thicknesses T3 can be about 2 mm.

The first outer shim 102, the second outer shim 108, and the inner shims 114 can be rotatably coupled together at their respective first ends 104, 110, and 116 with a suitable coupling mechanism 120 to allow each of the shims 102, 108, and 114 to rotate with respect to and independent of the other shims about an axis of rotation R. The ability of the shims to rotate independently about the axis of rotation R allows the surgeon to quickly and easily adjust an effective thickness of the feeler gauge and alignment device 100 when evaluating a gap in the resected knee joint 50.

The feeler gauge and alignment device 100 further includes a locking feature 121 structured for releasably locking selected ones of the shims together to prevent movement of the shims when evaluating the gap in the resected knee joint 50. Additional details regarding the locking feature 121 will be described below with reference to FIG. 12.

In order to assist with the evaluation of a resection gap, the first outer shim 102 can be provided with a first measurement key 122 and the second outer shim 108 can be provided with a second measurement key 124. As will be discussed in further detail below, the first outer shim 102 can be used as the "default" starting point for measuring a resection gap with the patient's knee joint 50 in a position of extension, as illustrated by the extension identifier 123. The second outer shim 108 can be used as the "default" starting point for measuring another resection gap with the patient's knee joint 50 in a position of flexion, as illustrated by the flexion identifier 125.

With reference to FIG. 9, the first line 126 in the measurement key 122 represents the thickness T1 of the first outer shim 102, which in the present example is 8 mm. The second line 128 in the measurement key 122 represents the thickness T3 of the inner shim 114A, which in the present example is 2 mm. The third and fourth lines 130 and 132 in the measurement key 122 represent the thicknesses T3 of the inner shims 114B and 114C, which in the present example are also 2 mm. Thus, according to the first measurement key 122, the user can easily and quickly determine that the effective thickness of the feeler gauge and alignment device 100 with the first outer shim 102 alone is 8 mm; the effective thickness of the feeler gauge and alignment device 100 with the first outer shim 102 and one inner shim 114A is 10 mm; the effective thickness of the feeler gauge and alignment device 100 with two inner shims 114A and 114B is 12 mm; and the effective thickness of the feeler gauge and alignment device 100 with the first outer shim 102 and all three inner shims 114A-114C is 14 mm. As will be described in further detail below, the effective thickness of the feeler gauge and alignment device 100 in extension can be used to determine the appropriate size of implant for insertion into the patient's knee joint 50.

With reference to FIG. 10, the first line 134 in the measurement key 124 can represent the thickness T2 of the second outer shim 108, which in the present example is 6 mm. However, as depicted in FIG. 10, the first line 134 reads 8 mm. In one example, it can be advantageous not to replace the exact amount of bone posteriorly (i.e. in flexion), and instead leave a small gap on the order of a few millimeters to prevent the surgeon from over tightening the knee joint in flexion. Over tightening the joint can lead to anterior cruciate ligament (ACL) avulsion. In order to institute the desired gap, the "8 mm shim" is instead set to 6 mm in the present example (i.e., cutting 2 mm extra compared to the implant). However, it should be understood that the foregoing "gap creation" means is not a necessary feature of the feeler gauge and alignment device 100. The various thicknesses and measurement scheme are presented for purposes of example and not limitation.

With further reference to FIG. 10, the second line 136 in the measurement key 124 represents the thickness T3 of the inner shim 114C, which in the present example is 2 mm. The third and fourth lines 138 and 140 in the measurement key 124 represent the thicknesses T3 of the inner shims 114B and 114A, which in the present example are also 2 mm. Thus, according to the second measurement key 124, the user can easily and quickly determine that the effective thickness of the feeler gauge and alignment device 100 with the second outer shim 108 alone is 8 mm; the effective thickness of the feeler gauge and alignment device 100 with the second outer shim 108 and one inner shim 114C is 10 mm; the effective thickness of the feeler gauge and alignment device 100 with the second outer shim 108 and two inner shims 114C and 114B is 12 mm; and the effective thickness of the feeler gauge and alignment device 100 with the second outer shim 108 and all three inner shims 114C-114A is 14 mm. As will be described in further detail below, the effective thickness of the feeler gauge and alignment device 100 in flexion can be used to determine the appropriate size of implant for insertion into the patient's knee joint 50.

As illustrated in FIGS. 9 and 10, the first outer shim 102, the second outer shim 108, and the inner shims 114 each include an alignment aperture 131 extending therethrough. The alignment apertures 131 can be positioned on the shims such that when two or more of the shims 102/108 and 114 are stacked together and aligned, the corresponding apertures 131 form an alignment channel that can receive an alignment rod for verifying a leg alignment and thus, proper correction of the patient's knee. In one example, the alignment channel includes an alignment axis extending therethrough that is substantially parallel to the axis of rotation R. The alignment apertures 131 are shown as generally circular merely for purposes of example and not limitation. In other examples, the alignment apertures 131 can take on any suitable shape that is compatible with the cross-sectional shape of the alignment rod.

Figure 11:
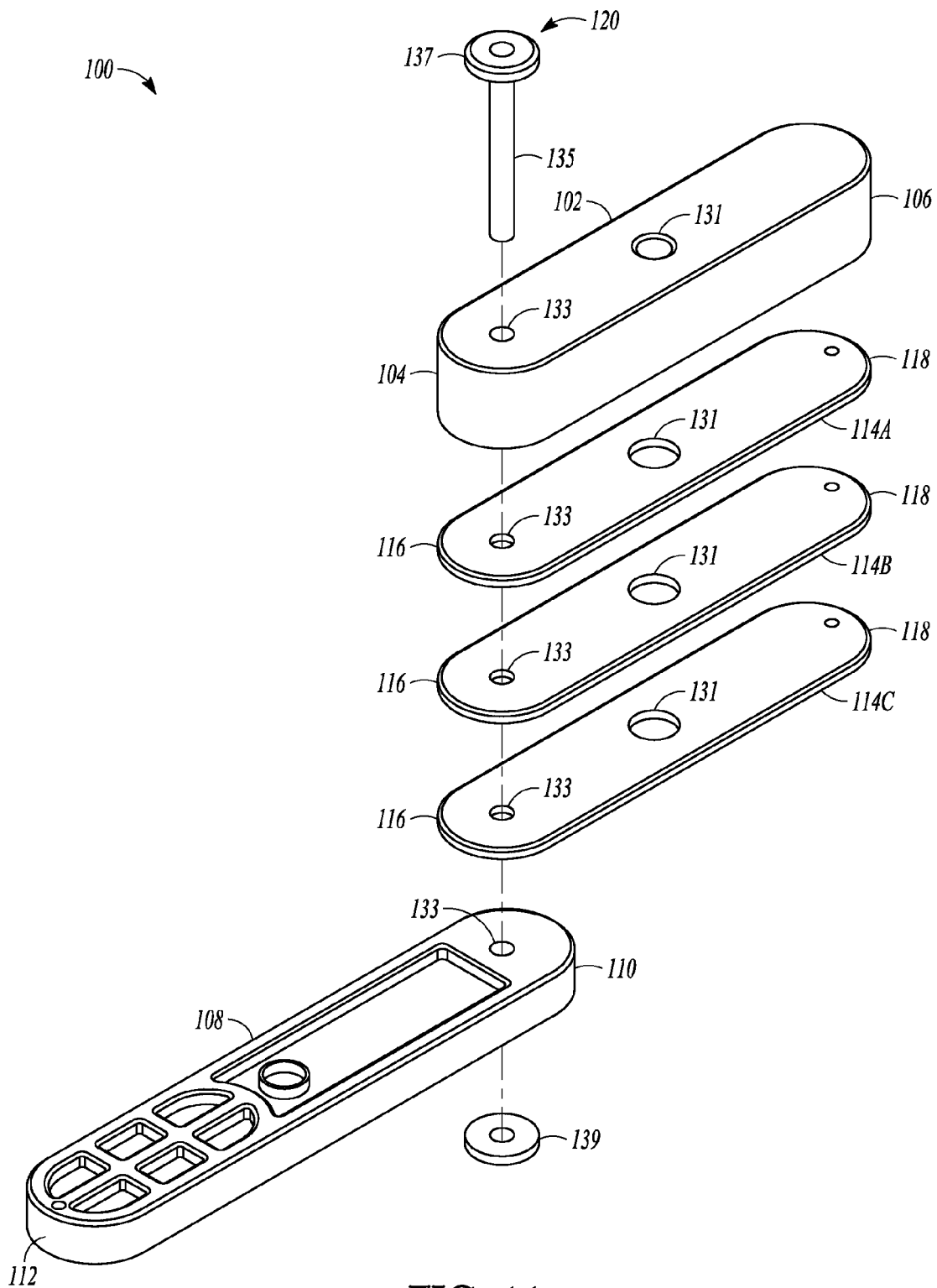
FIG. 11 is an exploded perspective view of the feeler gauge and alignment device of FIGS. 9 and 10.

FIG. 11 is an exploded perspective view of the feeler gauge and alignment device 100. As illustrated in FIG. 11, the first outer shim 102, the second outer shim 108, and the inner shims 114 each include a coupling aperture 133 adjacent to their respective first ends 104, 110, and 116. The coupling apertures 133 can be designed to align when the first outer shim 102, the second outer shim 108, and the inner shims 114 are stacked as illustrated in FIGS. 9 and 10 such that the coupling mechanism 120 can be inserted through a coupling channel formed by the apertures 133.

As illustrated in FIGS. 9-11, in one example the coupling mechanism 120 can include a generally cylindrical shaft 135, a first shoulder member 137 and a second shoulder member 139. When assembled, the cylindrical shaft 135 is received within the coupling channel formed by the series of apertures 133, the first shoulder member 137 is positionable adjacent to an outer surface 141 of the first outer shim 102, and the second shoulder member 139 is positionable adjacent to an outer surface 142 of the second outer shim 108. The distance between the first and second shoulder members 137 and 139 can be slightly larger than the combined thicknesses of the first outer shim 102, the second outer shim 108, and the inner shims 114 to allow rotation of the shims about the axis of rotation R as discussed above.

A coupling mechanism structured as a cylindrical shaft with two opposing shoulder members is merely one example of a coupling mechanism that can be used to rotatably couple the shims of a feeler gauge and alignment device. Thus, any suitable coupling mechanism 120 can be used that allows rotation of the shims about a center of rotation including, but not limited to, a rivet, pin, bolt, or the like.

Figure 12:
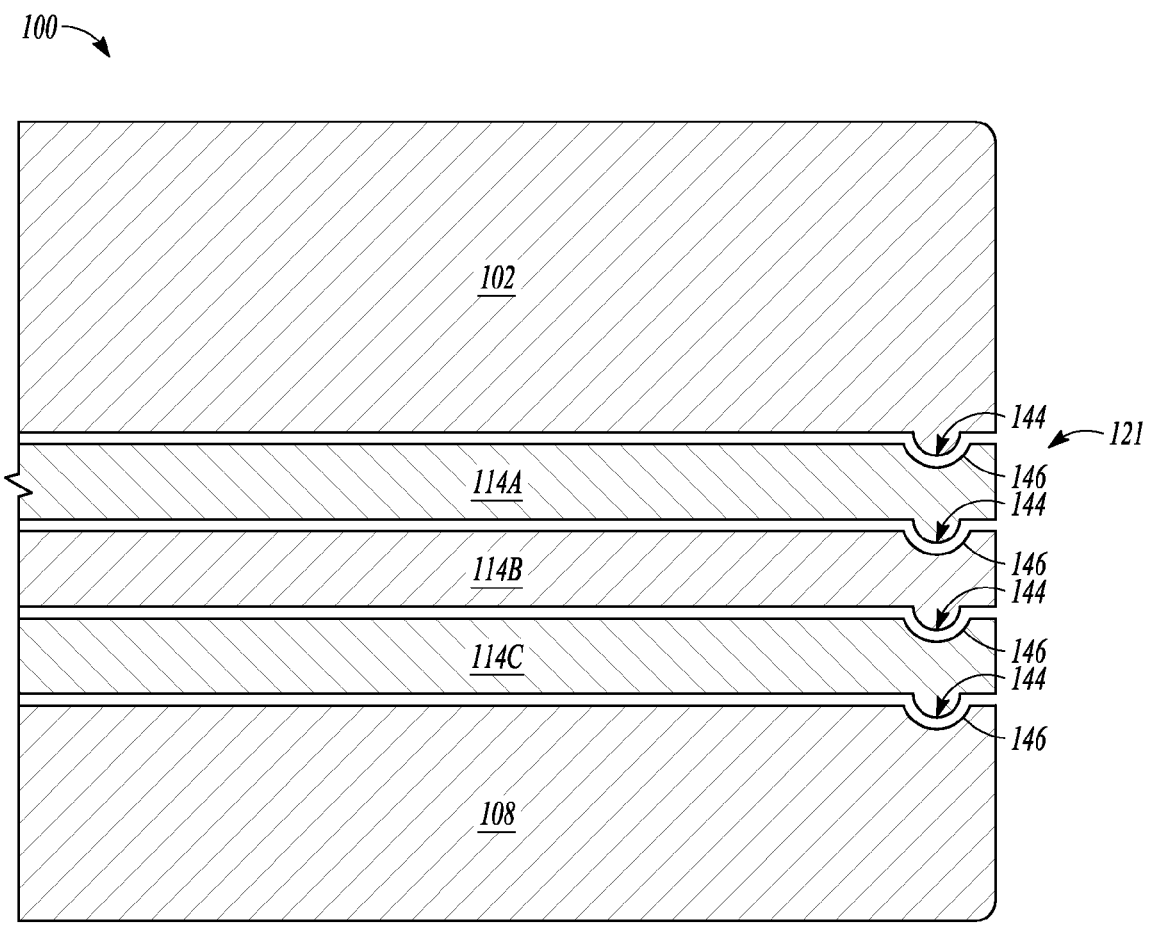
FIG. 12 is a cross sectional view of a portion of the feeler gauge and alignment device illustrating one example of a locking feature.

FIG. 12 is a cross sectional view of a portion of the feeler gauge and alignment device 100 illustrating one example of the locking feature 121. As shown in FIG. 12, the locking feature 121 comprises a series of protrusions 144 and recesses 146 on adjacent shims. For example, when the first outer shim 102 is rotated and aligned with the inner shim 114A, the protrusion 144 extending from a bottom surface of the shim 102 is received within and engages the recess 146 in a top surface of the shim 114A. Adjacent shims can be separated such as by simply pulling or pushing the shims in opposing directions, thus releasing the protrusion 144 from the recess 146. In one example, the protrusions 144 have a rounded or semicircular protruding outer surface and the recesses 146 have a complementary rounded or semicircular recessed surface. The rounded or semicircular surfaces allow the protrusion 144 to slide out of the recess 146 during separation. However, corresponding protrusions and recesses having any shape, whether rounded or non-rounded, can be used without departing from the intended scope of the present patent application. In an example, the protrusions 144 and the recesses 146 have a generally square cross-sectional shape. Further, in an example, the protrusions 144 can be structured as cylindrical pins that are receivable within complementary recesses 146.

The positioning of the protrusions 144 and the recesses 146 on the shims can be reversed while maintaining the desired functionality. Further, the locking feature 121 is not limited to a series of protrusions 144 and recesses 146. Rather, any suitable locking feature can be used such as, for example, snaps, a hook-and-loop type fastener, friction fit, an adhesive, or the like.

Figure 13:
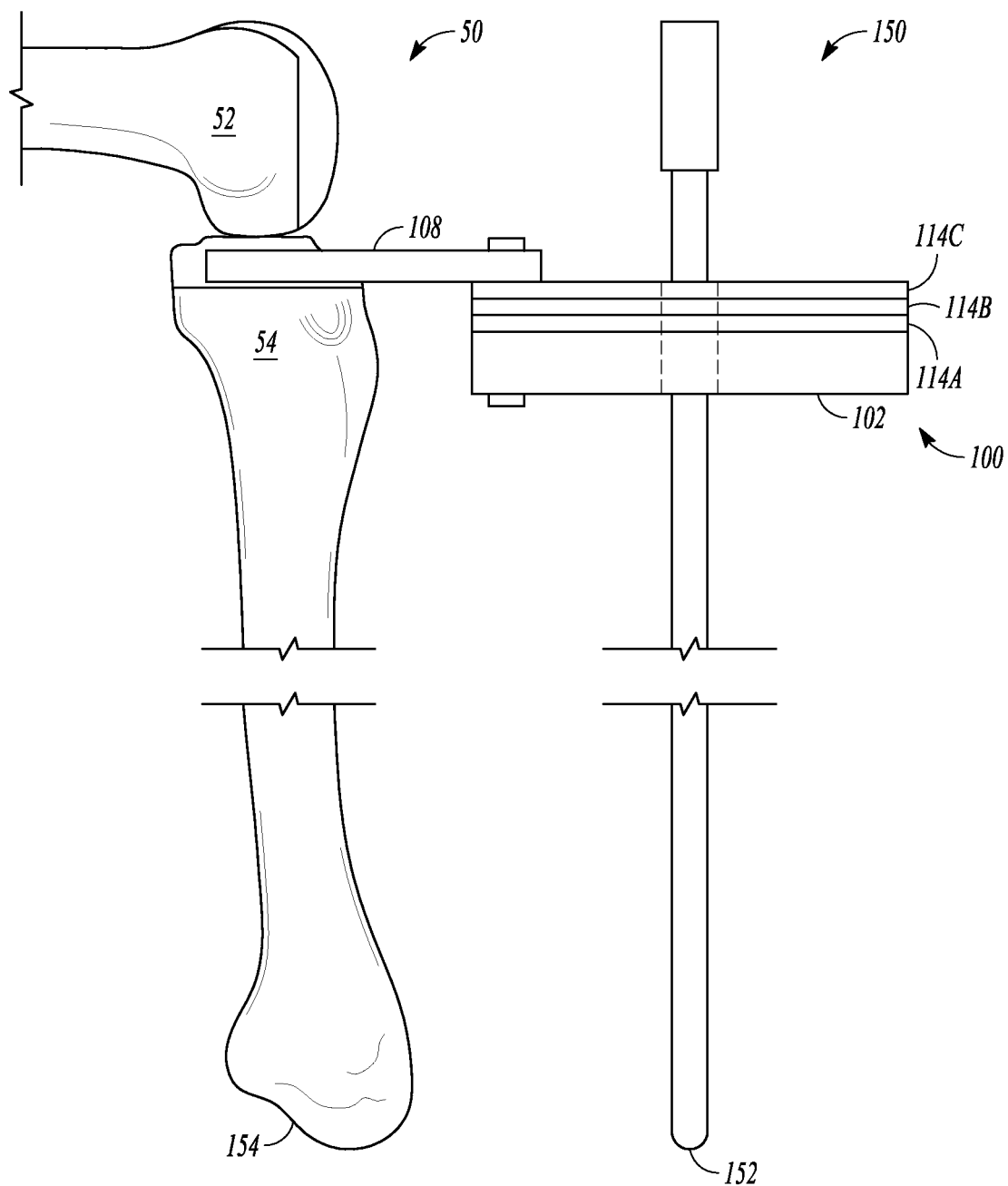
FIGS. 13-17 illustrate an example of a method of using the feeler gauge and alignment device in accordance with the present patent application.
Figure 14:
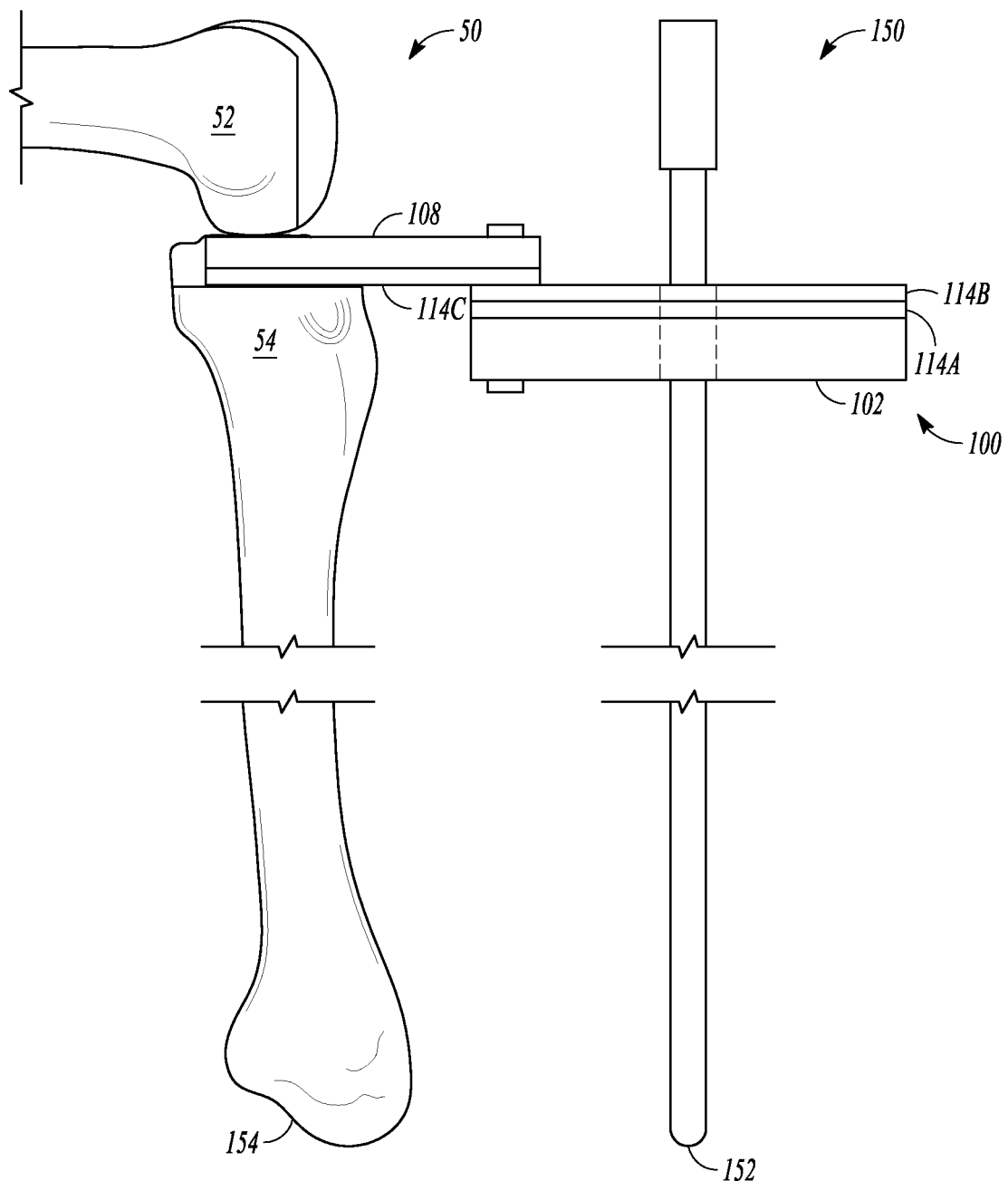
Figure 15:
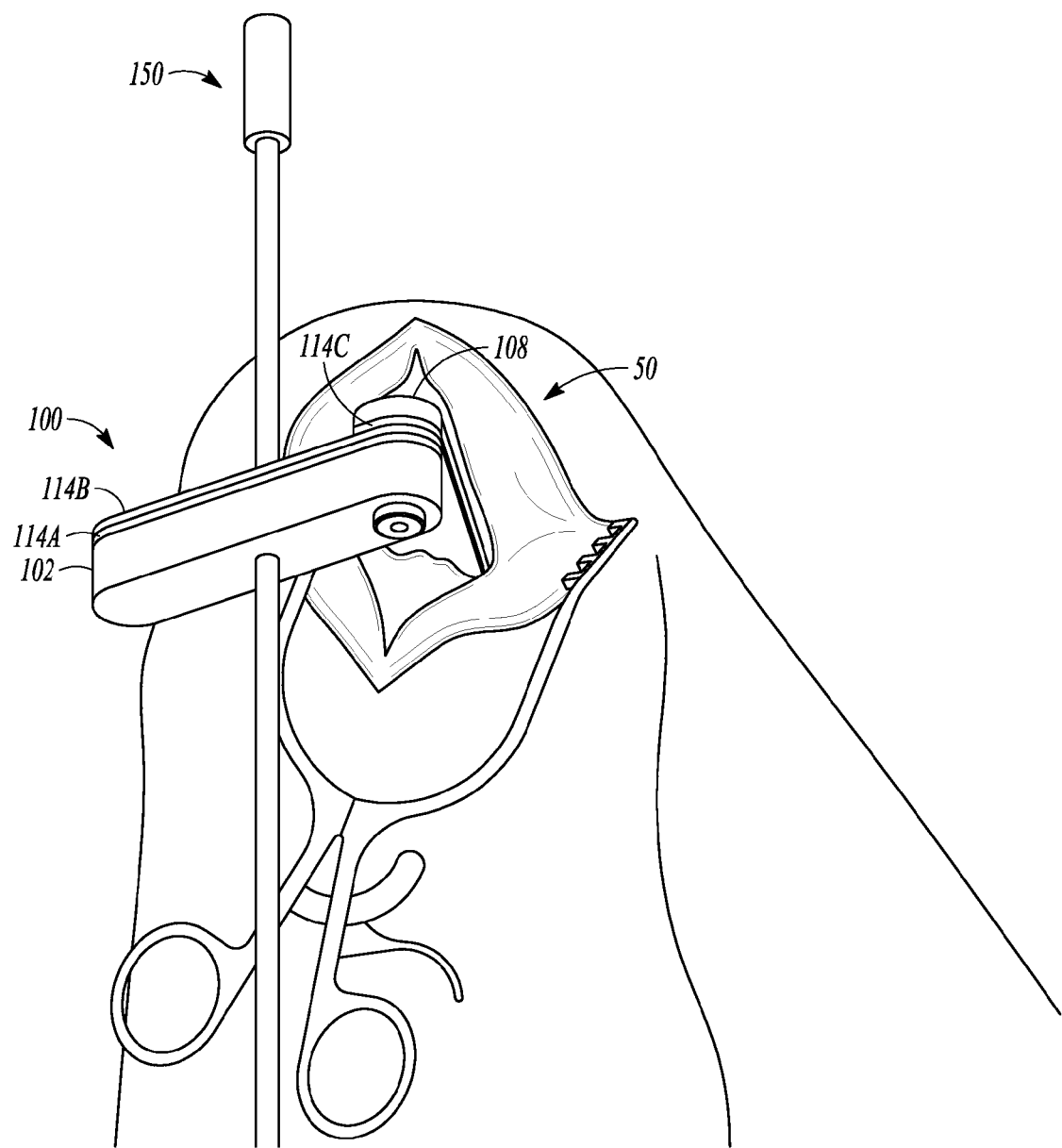
Figure 16:
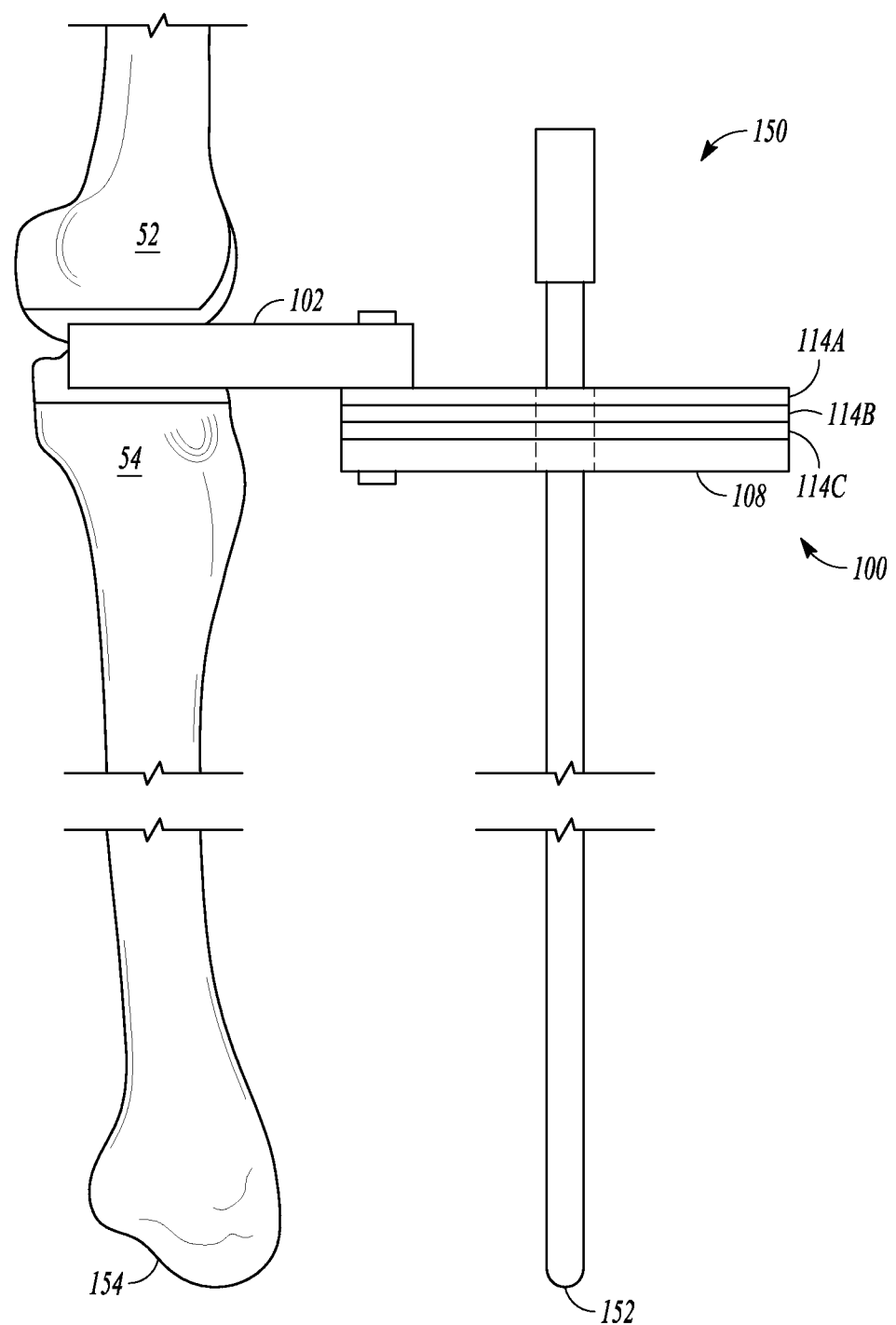
Figure 17:
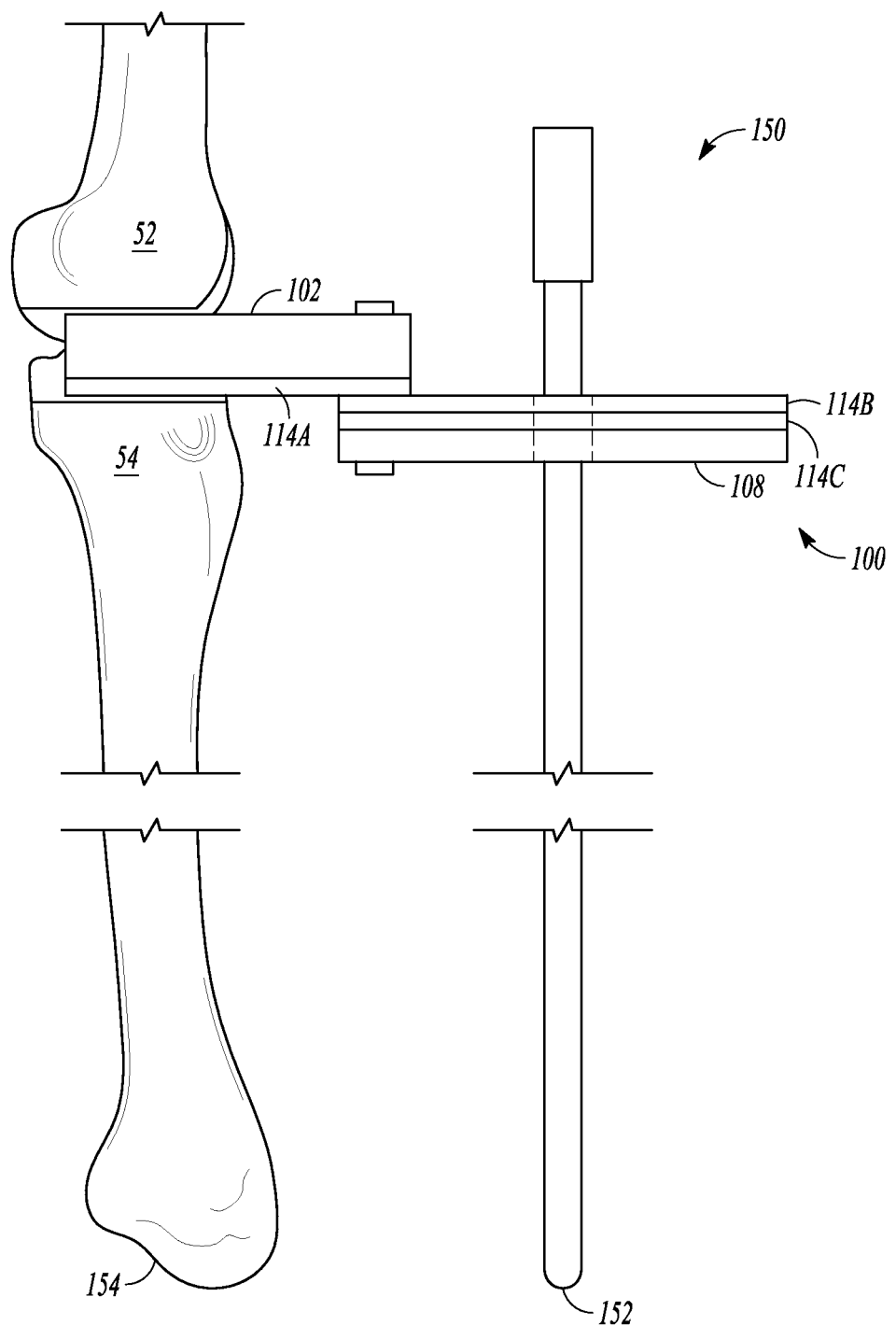

FIGS. 13-17 illustrate an example of a method of using the feeler gauge and alignment device 100 during a surgical procedure or diagnosis. Particularly, FIGS. 13-15 illustrate exemplary steps in measuring a gap between the resected tibia surface and the femur 52 and verifying a desired alignment of the knee joint 50 with the knee in flexion, while FIGS. 16-17 illustrate exemplary steps in measuring a gap between the resected tibia surface and the resected femur surface and once again verifying the desired alignment of the knee joint 50 with the knee in extension. However, the measurement and alignment method can alternatively begin with measuring the extension gap followed by measuring the flexion gap.

With reference to FIG. 13, the surgeon begins by inserting the second outer shim 108 into the resected knee joint 50 with the knee in flexion. If the second outer shim 108 fits snug without being too difficult to insert, then the thickness of the second outer shim 108 accurately simulates the proper thickness of the tibial replacement component in flexion, as represented by the second measurement key 124 of FIG. 10. However, if the second outer shim 108 does not fit snug within the resected knee joint 50, then the surgeon can remove the second outer shim 108, rotate and lock the inner shim 114C to the second outer shim 108, and reinsert the feeler gauge and alignment device 100 into the knee as illustrated in FIG. 14. Thus, in operation the surgeon can insert progressively thicker shims into the resection gap and repeat the gap checking.

As illustrated in FIG. 14, the feeler gauge and alignment device 100 now fits snugly within the resected knee joint 50. Thus, the combined thickness of the second outer shim 108 and the inner shim 114C accurately simulates the proper thickness of the tibial replacement component in flexion, as represented by the second measurement key 124 of FIG. 10. After measuring the gap, the surgeon can insert an alignment rod 150 into the alignment channel formed by the alignment apertures 131 in the first outer shim 102 and the inner shims 114A and 114B. Proper alignment of the knee joint 50 can be verified such as by ensuring alignment of a distal end 152 of the alignment rod 150 with the center of the patient's ankle adjacent to a distal end 154 of the tibia 54. In order to accurately verify the alignment of the distal end 152 of the alignment rod 150 with the center of the ankle, the first outer shim 102 and the inner shims 114A and 114B can be rotated as illustrated in FIG. 15 such that the shims are positionable adjacent to the patient's knee joint 50.

Turning next to FIG. 16, the surgeon continues the measurement and alignment process by inserting the first outer shim 102 into the resected knee joint 50 with the knee in extension. If the first outer shim 102 fits snug without being too difficult to insert, then the thickness of the first outer shim 102 accurately simulates the proper combined thickness of the tibial and femoral replacement components in extension, as represented by the first measurement key 122 of FIG. 9. However, if the first outer shim 102 does not fit snug within the resected knee joint 50, then the surgeon can remove the first outer shim 102, rotate and lock the inner shim 114A to the first outer shim 102, and reinsert the feeler gauge and alignment device 100 into the knee as illustrated in FIG. 17.

As illustrated in FIG. 17, the feeler gauge and alignment device 100 now fits snugly within the resected knee joint 50. Thus, the combined thickness of the first outer shim 102 and the inner shim 114A accurately simulates the proper combined thickness of the tibial and femoral replacement components in extension, as represented by the first measurement key 122 of FIG. 9. After measuring the gap, the surgeon can insert the alignment rod 150 in the alignment channel formed by the alignment apertures 131 in the second outer shim 108 and the inner shims 114B and 114C. Once again, proper alignment of the knee joint 50 can be verified such as by ensuring alignment of the distal end 152 of the alignment rod 150 with the center of the patient's ankle adjacent to the distal end 154 of the tibia 54. Similar to the discussion above with reference to FIG. 15, the second outer shim 108 and the inner shims 114B and 114C can be rotated toward the patient's knee joint 50 when verifying the proper alignment.

The feeler gauge and alignment device 100 is illustrated and described as including three inner shims 114A-114C for purposes of example and not limitation. Thus, any number of inner shims can be incorporated into the feeler gauge and alignment device 100 without departing from the intended scope of the present patent application.

Additionally, the various shim thicknesses were described merely for purposes of example and illustration. Thus, the shims can be designed with any suitable thickness, and that thickness can be adjusted to match the desired accuracy resolution that is necessary for the application. Further, it is not necessary to provide shims of different thicknesses. In an example, the feeler gauge and alignment device includes a plurality of shims having the same thickness, such as about 2 mm. Providing a first outer shim 102 and/or a second outer shim 108 having a greater thickness than the inner shims 114 allows the surgeon to begin the gap checking procedure with a shim having a greater thickness to obtain a "rough" fit and then "fine tune" the fit with shims having a lesser thickness. However, the same goal of measuring a resection gap can be achieved without starting with a larger shim and instead using a plurality of stacked, smaller shims.

In an example, the feeler gauge and alignment device includes one of the first outer shim 102 or the second outer shim 108 in addition to the inner shims 114. In such example, the sole outer shim can be designed with a "universal" thickness that is suitable for use in measuring several different gaps, such as measuring gaps with the knee joint 50 in flexion or extension.

Furthermore, the feeler gauge and alignment device 100 can be manufactured using any suitable, biocompatible material. In one example, the first outer shim 102, the second outer shim 108, and the inner shims 114 can be formed from a medical-grade plastic. Other suitable materials can include, but are not limited to, stainless steel, silicone rubber, and the like.

Although the subject matter of the present patent application has been described with reference to various embodiments, workers skilled in the art will recognize that changes can be made in form and detail without departing from the scope of the invention recited in the below claims.

The claimed invention is:

1. A feeler gauge and alignment device comprising:
   a first outer shim having a first end, a second end, and an alignment aperture disposed between the first end of the first outer shim and the second end of the first outer shim;
   a second outer shim having a first end, a second end, and an alignment aperture disposed between the first end of the second outer shim and the second end of the second outer shim, wherein the first outer shim has a thickness that is different than a thickness of the second outer shim;
   a plurality of inner shims disposed between the first outer shim and the second outer shim, each of the plurality of inner shims having a first end, a second end, and respective first and second ends, wherein each of the plurality of inner shims has a thickness that is different than the thickness of the first outer shim and the thickness of the second outer shim, and wherein the thicknesses of the plurality of inner shims are identical to each other;

a coupling member structured for rotatably coupling the first outer shim, the second outer shim, and the plurality of inner shims about the respective first ends along an axis of rotation, wherein the alignment apertures of the first outer shim, the second outer shim, and the plurality of inner shims are spaced apart from the axis of rotation and include a common internal peripheral dimension;

an alignment rod configured to be received within an alignment channel defined by the alignment apertures in selected ones of the first outer shim, the second outer shim, and the plurality of inner shims, wherein the alignment channel includes an alignment axis extending therethrough that is parallel to the axis of rotation; and a locking feature for releasably locking selected ones of the first outer shim, the second outer shim, and the plurality of inner shims adjacent one another.

2. The feeler gauge and alignment device of claim 1, wherein the thicknesses of the first outer shim, the second outer shim, and each of the plurality of inner shims are constant between the respective first and second ends.

3. The feeler gauge and alignment device of claim 1, wherein the coupling member extends within a coupling channel defined by a plurality of coupling apertures, one of the plurality of coupling apertures adjacent each of the first ends of the first outer shim, the second outer shim, and the plurality of inner shims.

4. The feeler gauge and alignment device of claim 3, wherein the coupling member includes a shaft positioned within the coupling channel, a first shoulder member positioned adjacent to an outer surface of the first outer shim, and a second shoulder member positioned adjacent to an outer surface of the second outer shim.

5. The feeler gauge and alignment device of claim 1, wherein the alignment rod is structured for insertion into the alignment channel such that the alignment rod extends perpendicular to an outer surface of the first outer shim and an outer surface of the second outer shim.

6. The feeler gauge and alignment device of claim 1, wherein the first outer shim, the second outer shim, and the plurality of inner shims are formed from plastic.

7. The feeler gauge and alignment device of claim 1, further comprising a measurement key displayed on at least one of the first outer shim, the second outer shim, and the plurality of inner shims, the measurement key indicating the thicknesses of the first outer shim, the second outer shim, and the plurality of inner shims.

* * * * *

UNITED STATES PATENT AND TRADEMARK OFFICE
CERTIFICATE OF CORRECTION

| | | |
|---|---|---|
| PATENT NO. | : 8,663,234 B2 | Page 1 of 1 |
| APPLICATION NO. | : 13/195604 | |
| DATED | : March 4, 2014 | |
| INVENTOR(S) | : Grimm et al. | |

It is certified that error appears in the above-identified patent and that said Letters Patent is hereby corrected as shown below:

In the Claims

In column 10, line 67, in Claim 1, after "and", insert --an alignment aperture disposed between the--, therefor Signed and Sealed this
Fifth Day of August, 2014

Michelle K. Lee
*Deputy Director of the United States Patent and Trademark Office*